US010222309B2

(12) United States Patent
Engels et al.

(10) Patent No.: US 10,222,309 B2
(45) Date of Patent: Mar. 5, 2019

(54) APPARATUS AND METHOD FOR STATIC SEDIMENTATION TESTS COMPRISING A PLURALITY OF SEDIMENTATION CYLINDERS, WHICH ARE SUBJECT TO THE SAME MIXING CONDITIONS

(71) Applicant: Tailpro Consulting SpA, Santiago (CL)

(72) Inventors: Jonathan Engels, Santiago (CL); Peter Amelunxen, Santiago (CL)

(73) Assignee: Avoca Engineers SpA, Santiago (CL)

( * ) Notice: Subject to any disclaimer, the term of this patent is extended or adjusted under 35 U.S.C. 154(b) by 328 days.

(21) Appl. No.: 15/160,297

(22) Filed: May 20, 2016

(65) Prior Publication Data

US 2016/0356691 A1     Dec. 8, 2016

(30) Foreign Application Priority Data

Jun. 3, 2015    (CL) .................................. 2015-1499

(51) Int. Cl.
*B01D 21/01*      (2006.01)
*B01D 21/30*      (2006.01)
(Continued)

(52) U.S. Cl.
CPC .............. *G01N 15/04* (2013.01); *B01D 21/01* (2013.01); *B01D 21/30* (2013.01); *B01D 21/32* (2013.01);
(Continued)

(58) Field of Classification Search
CPC ........... G01N 15/04; G01N 2015/0092; B01D 21/01; B01D 21/30
See application file for complete search history.

(56) References Cited

U.S. PATENT DOCUMENTS

| | | |
|---|---|---|
| 2,411,092 A | 11/1946 | Hood |
| 3,954,342 A | 5/1976 | Boeke |

(Continued)

FOREIGN PATENT DOCUMENTS

CL            43863 B      3/2005

*Primary Examiner* — Paul M. West
(74) *Attorney, Agent, or Firm* — Fox Rothschild LLP

(57) ABSTRACT

The invention relates to an apparatus for static sedimentation tests comprising a plurality of sedimentation cylinders, which are subject to the same mixing conditions, said apparatus comprises:
  a. A variable number of transparent sedimentation cylinders, the most common being 12;
  b. Each sedimentation cylinder is located inside a non-intrusive emitter and receiving sensor housing where each housing has an electronic ID card, electronic circuit boards and connection to a control system;
  c. A support structure containing the sedimentation cylinders and sensor housings which rotates around an axis of rotation;
  d. Each sedimentation cylinder has a bottom stopper and top stopper;
  e. Where each bottom stopper of each sedimentation cylinder is mounted on a lateral bar parallel to the rotation axis, by a fixing to the supporting structure;
  f. Also the sedimentation cylinders are fixed in the supporting structure by a clamping system around the top stopper of each sedimentation cylinder
  g. The top stopper of each sedimentation cylinder has an additive injection system.
In addition, its presented a method for static sedimentation tests carried out simultaneously and under the same mixing conditions in a plurality of sedimentation cylinders, the most common being 12; which rotate around an axis of rotation; where each sedimentation cylinder is located inside a sensor housing which are connected to a control system.

23 Claims, 5 Drawing Sheets

(51) Int. Cl.
  *B01D 21/32*   (2006.01)
  *B01D 21/34*   (2006.01)
  *G01N 15/04*   (2006.01)

(52) U.S. Cl.
  CPC ....... *B01D 21/34* (2013.01); *G01N 2015/045* (2013.01)

(56) References Cited

U.S. PATENT DOCUMENTS

| | | |
|---|---|---|
| 4,318,296 A | 3/1982 | Parker et al. |
| 4,779,462 A | 10/1988 | Boullet et al. |
| 4,830,126 A | 5/1989 | Boullet |
| 4,976,871 A | 12/1990 | Banks et al. |
| 5,431,037 A | 7/1995 | Howard |
| 2016/0266023 A1* | 9/2016 | Gratiot .................. G01N 15/10 |

* cited by examiner

APPARATUS AND METHOD FOR STATIC SEDIMENTATION TESTS COMPRISING A PLURALITY OF SEDIMENTATION CYLINDERS, WHICH ARE SUBJECT TO THE SAME MIXING CONDITIONS

TECHNICAL FIELD

The proposed invention relates to the field of solid-liquid separation of slurries or pulps required in many small scale and large industrial processing applications, and looks for a total transformation of both how the separation tests are done and the method of collecting data and generating results, thanks to its control system. In addition to the field of solid-liquid separation, the same invention can be used in liquid-liquid separation applications where dense media separation occurs and can be determined through boundary condition identification.

The invention includes an apparatus for performing static sedimentation tests and a method for measuring sedimentation through static sedimentation tests, incorporating digital sensors specially programmed for this purpose, to obtain raw data and/or comparison parameters, generating the expected results.

PRIOR ART

Solid-Liquid Separation

Slurries, pulps or liquids with suspended particles are often required to have the suspended particles and process liquor (often referred to as supernatant liquid) separated. This process is often referred to as thickening or clarification and applies to multiple industries with the goal of recovering either the process liquor (supernatant) or the suspended particle material for reuse in the processing procedure, further processing, or disposal. During the thickening or clarification process, a slurry or pulp is continuously fed into a thickener, clarifier or settling tank device, where the suspended particles are allowed to settle under the influence of gravity to form a thickened mud bed on the bottom of the tank or vessel. This mud is normally referred to as an underflow, is removed, normally by a pump at the base of the tank or vessel, and either processed or disposed of. The process liquor, with minimal suspended particles, is removed from the top of the tank and is either discharged, reused in the industrial process or reprocessed in another clarification tank for further solid-liquid separation.

In a thickener, clarifier or settling tank, chemical products (principally, but not limited to, flocculants and coagulants) may be mixed with the slurry as it is fed into the tank. This is usually referred to as the feed-well of the tank where mixing occurs between the slurry and the additive that promote gravity sedimentation of the particles in the slurry to accumulate in the mud bed and be removed by the underflow pump. The underflow extraction point is normally centrally located at the bottom of the tank and the base of the tank is normally conical in shape incorporating a rake mechanism to push this thickened mud towards the extraction point. This provides continuous operations whereby thickened mud (underflow) and clarified liquor (overflow) are extracted while slurry to be treated (feed) is simultaneously mixed with a chemical additive and fed into the tank.

Liquid-Liquid Separation

The dense fraction separation of liquids is often required in many process fields to refine or purify a particular product or material. Oil refinery is a specific case whereby crude oil is separated into lighter fractions by the fractional distillation process. For this particular process, the density of the various extracted liquids, such as diesel, kerosene and gasoline vary and provide a form of distinguishing this property through dense fraction separation. There are many varieties and techniques of liquid-liquid separation specific to a particular process or methodology. Those whereby a boundary between different fractions can be visually distinguished or through emitted wavelength propagation characteristics, can benefit from the use of the presented invention to determine these boundary changes with time.

The invention is primarily targeted at the solid-liquid separation industry, but can be equally applied to liquid-liquid separation processes.

Settling Tests

There are several types of settling tests, the most common is mixing slurries in sedimentation cylinders measuring the height of the solids as the slurry settles.

Performing more than one sedimentation test simultaneously creates the challenge of ensuring that all sedimentations tests are carried out under the same condition and consequently, there are several solutions that now allow this. Particularly in the field of health, blood mixers are widely used, which consists of a machine containing tubes that rotate around an axis in order to mix the contents of each tube.

For the specific case of inorganic sedimentations, in particular in the field of mining, a similar system to the blood mixing system is used, except in the case of chilean patent CL43863, where two side brackets are sustaining the axis, instead of one, as is often used in blood mixers.

While at first glance the present invention may seem similar to the aforementioned Chilean patent, it presents substantial differences that make them distinct to each other.

In terms of form:

a. Patent CL43863 has two axes in the middle of horizontal plates (claim 1.C.), while the present invention has one axis at a greater height, in order to enable the apparatus to naturally return to the vertical position without manual intervention or need of a peg as described in claim 1.G. of said patent.

b. Patent CL43863 specifies that the tubes are located inside the frame (claim 1.D.) while the present invention contemplates a new orientation of tubes, which are alternately located laterally outside the frame or support structure, thus to reduce size and optimize efficiency. This new feature allows the use of many more tubes and is only possible because automatic sensors are used for measurement instead of traditional optical methods. Also, it allows to have enough space to install the control system and electronic parts, which is new with regard to what was presented in the chilean patent.

c. Patent CL43863 specifies from 1 to 10 tubes (claim 1.D.) while the present invention is designed for a variable number of tubes, the most common being 12, since in this way the new method of mixing allows measurement methods by using automatic sensors and not traditional optical methods, giving reliable results.

d. Patent CL43863 considers a crank (1.D.), while the present invention does not have this manual mechanism, since it considers an electro-mechanical mechanism programmed according to the desired results.

e. The proposed invention has housings that cover and/or surround each of the tubes/sedimentation cylinders and the measurement sensors, while Patent CL43863 has no housings since that it does not consider sensors and its associated measurement methodology.

f. In Patent CL43863 sedimentation occurs by gravity, while in the present invention, the system has a dosing device, which encourages sedimentation by supplying flocculants in the same apparatus.

In terms of substance:

Patent CL43863 discloses an instrument for doing simultaneous slurries settling tests, not including a method nor instruments for also measuring transparency of the liquid. In other words, the procedures and test methods are preserved intact. The present invention relates to a total transformation of both the manner in which the tests are conducted and the method in which data are collected through a custom program that generates immediate, computerized and reliable results by not having handling and manual interpretation. Given these characteristics, the differences mentioned are important and completely necessary to achieve the objective of this invention.

Chemical Additives

The principal chemical additives used in solid-liquid separation include flocculants, coagulants and ph-modifiers. Flocculants and coagulants are provided by many global chemical companies and often consist of a polymer molecular structure which agglomerates with suspended particles in a slurry to form flocculant chain structures, commonly referred to as flocs. These chains of particles settle faster than if the particles were separated and therefore increase the settling rate of the slurry within the thickener, clarifier or settling tank.

The properties of slurries and pulps are highly variable between process operations, and hence there are many types and combinations of flocculants and coagulants available on the market. Principally the molecular weight of the additive is varied, the charge, pH, unit cost and the physical form.

The performance of each type of additive is affected principally by the dilution of the slurry feed, the chemistry of the slurry (including, but not limited to, pH and oxidation-reduction potential), the dilution or preparation of the additive, and the dosage. For the thickener, clarifier and settling tank designers, the feed-well mixing also plays an important role in the performance of the system.

For liquid-liquid separation, a large variety of chemical additives can be applied depending on the properties and characteristics of a particular liquid under test.

As noted above, the invention described herein comprises an automatic flocculating dosing device for each sedimentation cylinder, as an important part of its structure, operation and method.

Identification of Additives and Dosage (Solid-Liquid Separation)

To identify the type of chemical additive to use in a solid-liquid separation, there are various styles of tests performed on a laboratory scale. The most common standard is a "jar-test" whereby a flask of known volume, containing slurry of a known solids mass and volume, is dosed with a chemical additive and mixed, normally by hand, and then the settling bed position is determined manually with a stopwatch and visual height reference, over a fixed period of time. The methodology to perform the test is an international standard as documented in the American Society for Testing Materials Norm ASTM D-2035. Data from the test is commonly interpreted using various methods, primarily the Kynch and Coe-Clevenger methods, which rely on the accuracy of the data collection to identify the optimum parameters of the chemical additives to be used in the full scale process operation.

The "jar-test" is considered a static settling test whereby the settled mud (underflow) and the liquor (overflow) are not removed during the test. It is becoming increasingly common that these static tests are used to identify the parameters to be verified with further small scale dynamic tests before implementation on a larger scale. These dynamic tests were developed to improve the prediction of the unit area defined by the static test, for the thickener, clarifier and settling tank as part of the design process.

Technology exists that can help to improve the "jar-test", concepts of which are discussed as per an optical device for monitoring the clarity of fluids as presented in U.S. Pat. No. 2,411,092 and later in U.S. Pat. No. 3,954,342 whereby the use of a light emitter and photodiode or receptor are disclosed to measure the clarity of fluids and display a unit of measurement on a readout. This type of technology is the common concept for turbidimeters and has since been modified over recent years to include light scattering sensors to improve its accuracy.

U.S. Pat. No. 4,976,871 teaches the use of an inline constant flow measurement of slurry using a light source and a photocell to be able to control flocculation dosing. This is a dynamic test that is used as a constant measuring device to identify the solids concentration of a flow of slurry in a stream.

U.S. Pat. No. 5,431,037 documents an inline control device consisting of a settling chamber that is installed adjacent to a thickener whereby a sample of overflow water from the thickener is drawn into a settling chamber to analyse the settling characteristics of the material and control the rate of addition of the flocculant to the thickener by the flocculant supply device, and therefore prevent excessive amounts of flocculant or increase the dosage depending on the clarity of the overflow water. The control device is designed for a continual operation to effectively verify the operation of the thickener and better control the flocculant dosage. The settling chamber draws a sample from the thickener via vacuum into the chamber until the liquid reaches two height probes, whereby the vacuum valve is closed and a timer starts. As the particulates in the liquid sample settle, a single light beam fixed to one side of the chamber then strikes a single photoelectric cell on the opposite side which stops the timer for a certain reading. The electronic control circuit uses this time in an algorithm to produce an output signal to control the flocculant addition to the thickener. The chamber empties, is washed by an input valve and the process automatically repeated as part of the continual operation of the thickener. The light source and photocell are used to determine an acceptable clarity of water based on the drawn overflow water obtained from the thickener to control the flocculant dosing and improve the clarity of the overflow water recovered from the thickener. The light source and photocell are not used to measure the settling velocity of a slurry or pulp, how this changes with time, the clarity of the water over different heights within the chamber during the settling test, a final mud bed depth and volume after a specific time nor produce data for interpretation of solid-liquid settling rates for sizing a thickener, clarifier or settling tank.

The previous described patent is based on almost the same principal as a prior art documented in U.S. Pat. No. 4,318,296 where a single photodiode and photocell are used in a settling cylinder to measure fixed position clarity of a liquid and thereby control the flocculation delivery within a settling tank.

U.S. Pat. No. 4,779,462 documents an apparatus for automatically measuring the apparent density of a mud or sludge contained in a liquid and the automatic measurement of the Ponsar Index. As part of the apparatus, a cylinder is used that is filled with 1.5 liters of clarified liquid that is then filled with 1 liter of mud containing water that is allowed to settle for a period of 30 minutes which is required to determine a parameter associated with the calculation of the Ponsar Index. A stepper motor controls a single or series of photodiodes and a single photocell that is located on the opposite side of the cylinder. The stepper motor moves the photodiodes and photocell up and down the cylinder to identify the position of the settled mud bed after the 30 minute period of time, and with the number of steps made by the motor, the apparatus can calculate the height and therefore the volume of settled mud over this fixed time period.

The photodiodes and photocell only calculate the volume of mud after the 30 minute period to report the volume parameter of the mud as part of the calculations of the entire operation of the apparatus. No real-time settling rate behaviour of the slurry and the use of chemical additives are considered. One of the inventors of this patent was granted U.S. Pat. No. 4,830,126 which is a modified apparatus to determine the Ponsar Index, and includes the same said settling cylinder, but considering a screw device to move the photodiodes and photocell after the 30 minute period.

Automatic control and optimized operation of the static "jar-test" style of measurement of solid-liquid separation of slurries has been a continuing concern of chemical additive vendors as well as settling equipment manufactures. The "jar-test" was first standardised by ASTM in 1999 to reduce result variability and define a test methodology.

However, no alternative standard currently exists. This is the subject of the current invention and the goal of the inventors, transform the way of performing tests by using a method of data collection that reduces errors and which through a program, delivers results, data or parameters digitized. Therefore, the aforementioned invention can be applied to provide precise, real-time control and monitoring of such settling tests to meet industrial needs as well as the possibility to standardise this type of test.

SUMMARY OF INVENTION

1. Objectives
    Transform the way in which solid-liquid or liquid-liquid sedimentation tests are done in order to reduce human error and increase the frequency, precision and accuracy of the data by an apparatus and method that using a custom programmation generates immediate, computerized and reliable results.
    Allow the simultaneous testing and data collection of multiple samples, considering the same standardised operating conditions and test parameters.
    Reduce the labour intensity associated with the prior art to allow more tests to be performed under different additives, dosages, dilutions and densities, thereby producing more test data in a given time frame.
    Allow a third party to remotely access and interpret the data from the settling tests by applying custom models, together with (but not limited to) known models such as the Kynch and Coe-Clevenger models for solid-liquid separation, for comparative analysis and reporting.
    Optimisation of thickeners, clarifiers, settling tanks and similar equipment including the operating conditions, chemical reagent dosages, and slurry or liquid chemistry used for industrial phase separation processes, including but not limited to the improvement of clarity of recovered liquor, reduction of additive dosages and consumptions costs, and the reduction of slurry or density specific liquid contamination.
2. Technical Problem
    Perform various sedimentation tests under the same conditions and with a methodology for electronic characterization of the behaviour of sedimentation.
Solution to Problem The concerns or limitations regarding the prior art of static settling tests (principally the "jar-test" for solid-liquid separation) are overcome with the presented invention that transforms data collection by a method that removes manual interaction and measurement, allowing tests to be run in parallel thus duplicating the same conditions, and allowing computational statistical analysis of the results both during and after the test is conducted.

The invention further allows multiple sedimentation cylinders to be installed (normally 12) located externally in a frame or structure that rotates, mixing each sedimentation cylinder under the same mixing conditions. This is an automated mixing mechanism that ensures all future tests can be performed under the same mixing conditions. Each sedimentation cylinder is fitted with a housing that incorporates emitter and receiving sensors, which can be sensors to sense mud bed position, final mud bed height, solids density, liquid density and clarity of the liquor. Receiving sensors are selected from the group comprising: photosensors, but can also be based on IR, UV, or optical sensitivity depending on the wavelength of the emitter device. Emitter sensors are selected from the group comprising: Light Emitting Diode (LED), IR, UV, laser or fixed/variable wavelength emitter.

Preferably, each housing is fitted with a minimum of four wavelength emitting sensors and four wavelength receiving sensors, facing each other and spaced at varying distances (depending on the type of the material under test) along the body of the housing, connected to a control system, to allow interpretation of the data successfully, although eight or more sensors are preferred, to allow higher measurement precision of the mud bed position and/or consolidation over time, or for liquid-liquid separation, the interfaces between two liquids with different densities over time. The housing fits over a custom transparent sedimentation cylinder with stoppers where the slurry, pulp or liquids are contained during the mixing and settling process. In addition, each housing has a chemical additives injection system as flocculants that are part of the structure and are an essential part of the apparatus and method by directly influencing sedimentation and results delivered, unlike only sedimentation by gravity.

The sensors are non-intrusive, incorporated directly in the housing design, and are connected to a control system, which records information of each sensor relative to the mud bed position, and/or her consolidation within time or the interfaces between two liquids with different densities. Furthermore, each sedimentation cylinder has the option to have a sensor installed within the slurry to measure the pH, temperature, oxidation reduction potential, and conductivity depending on the requirements of the test.

The control system collects and interprets data delivered by sensors; further it provides the status of the sensors during sedimentation tests. Moreover also communicates, processes, records and stores data from sensors in real time.

The control system, preferably but not limited to a small and portable Linux operating system, is coded with custom software, developed as part of the invention. The operating system is self-contained and connected to a screen or touchscreen, with input devices as preferred by the user (commonly an optical device and keyboard).

The control system and said custom software are designed to receive all sensor outputs at predetermined time intervals. These time intervals may be shorter during the first few minutes from the start of the settling tests and increase with time as required. The data is generated in real-time, stored locally, transmitted to a remote computer or server and subsequently used to provide feedback to the user prior to, during and after the settling test process. Using the data inputs from the sensors described as part of the invention, various analysis techniques are performed, including but not limited to signal processing, statistical analysis, rule-based processing including fuzzy, discrete, or heuristic logic, data management, pattern and series recognition, categorical analysis, or a combination thereof. The software of the control system can be modified or varied based on user input and subject to any preferred analytical method to be implemented.

The control system activates various control devices during operation, including but not limited to the mixing of the slurry or liquids within the tubes; the injection of chemical additives, flocculants or coagulants; sensor control; interaction with a Human Machine Interface (HMI); and the storage, transmission and reception of data and information.

The HMI is to allow information regarding the origins and physico-chemical properties of the slurry, information related to the type and quantity of each chemical additive, feedback to the user on the current status of the test, error detection and/or alarming, tube readiness and/or test completion, and data integrity and/or storage.

3. Advantageous Effects of the Invention

The method and apparatus are principally designed for solid-liquid separation of laboratory through to pilot scale testing of slurries and pulps to identify operational parameters for full scale thickeners, clarifiers and settling tank equipment. The advantageous effects of the invention are the transformation in the data collection and hence the accuracy is improved, by reducing test errors through removing manual interaction. This allows for a better comparison of data between tests performed on the same pulps while varying the characteristics of the additives used. This could engender the following advantages to the global solid-liquid separation field:

Optimization of selection of additive type, dose and preparation.

Optimization of recovery and clarity of liquor through correct additive selection and operational parameter identification.

Reduction of additive consumption and cost.

Reduction of slurry or pulp contamination through excess dosing.

Improvement of accuracy and precision of rheological testing of the settled solids.

Possibility of having accurate data/results in real time and accessed remotely.

Removal of manual errors in data collection

DETAILED DESCRIPTION OF THE INVENTION

The invention relates to an apparatus for static sedimentation tests comprising a plurality of sedimentation cylinders, which are subject to the same mixing conditions, said apparatus comprises:

a. A variable number of sedimentation cylinders, the most common being 12 transparent sedimentation cylinders;

b. Each sedimentation cylinder is located inside a non-intrusive emitter and receiving sensor housing where each housing has an electronic ID card, electronic circuit boards and connection to a control system;

c. A support structure containing the sedimentation cylinders and sensor housings which rotates around an axis of rotation;

d. Each sedimentation cylinder has a bottom stopper and top stopper;

e. Where each bottom stopper of each sedimentation cylinder is mounted on a lateral bar parallel to the rotation axis, by a fixing to the supporting structure;

f. Also the sedimentation cylinders are fixed in the supporting structure by a clamping system around the top stopper of each sedimentation cylinder;

g. The top stopper of each sedimentation cylinder has an additive injection system.

Also, there is a method for static sedimentation tests, carried out at the same time and under the same mixing conditions in a plurality of sedimentation cylinders, comprising:

(i) Add a solution which sedimentation tests generally require to be performed on a variable number of sedimentation cylinders, the most common being at least 12 transparent sedimentation cylinders, where each sedimentation cylinder is located inside a non-intrusive emitter and receiving sensor housing that is supported in a support structure which rotates around an axis of rotation and each sedimentation cylinder has a bottom stopper and top stopper, where the top stopper has an additive injection system;

(ii) Rotate the sedimentation cylinders around an axis of rotation to homogenise the solutions in each sedimentation cylinder;

(iii) Stop the sedimentation cylinders in an upright position and add chemical additives to each sedimentation cylinder, through the additive injection system;

(iv) Rotate again the sedimentation cylinders around the axis of rotation, for mixing the solutions and additives;

(v) Stop the sedimentation cylinders in an upright position;

(vi) Start the sedimentation test;

where all data from sedimentation tests and data delivered by each non-intrusive sensors with respect to mud bed position and/or consolidation time, final mud bed height, solids density, liquid density or clarity of the liquor are recorded by a control system.

Exemplary embodiments of the present invention are demonstrated hereinafter with reference to the accompanying figures.

Figure 1:
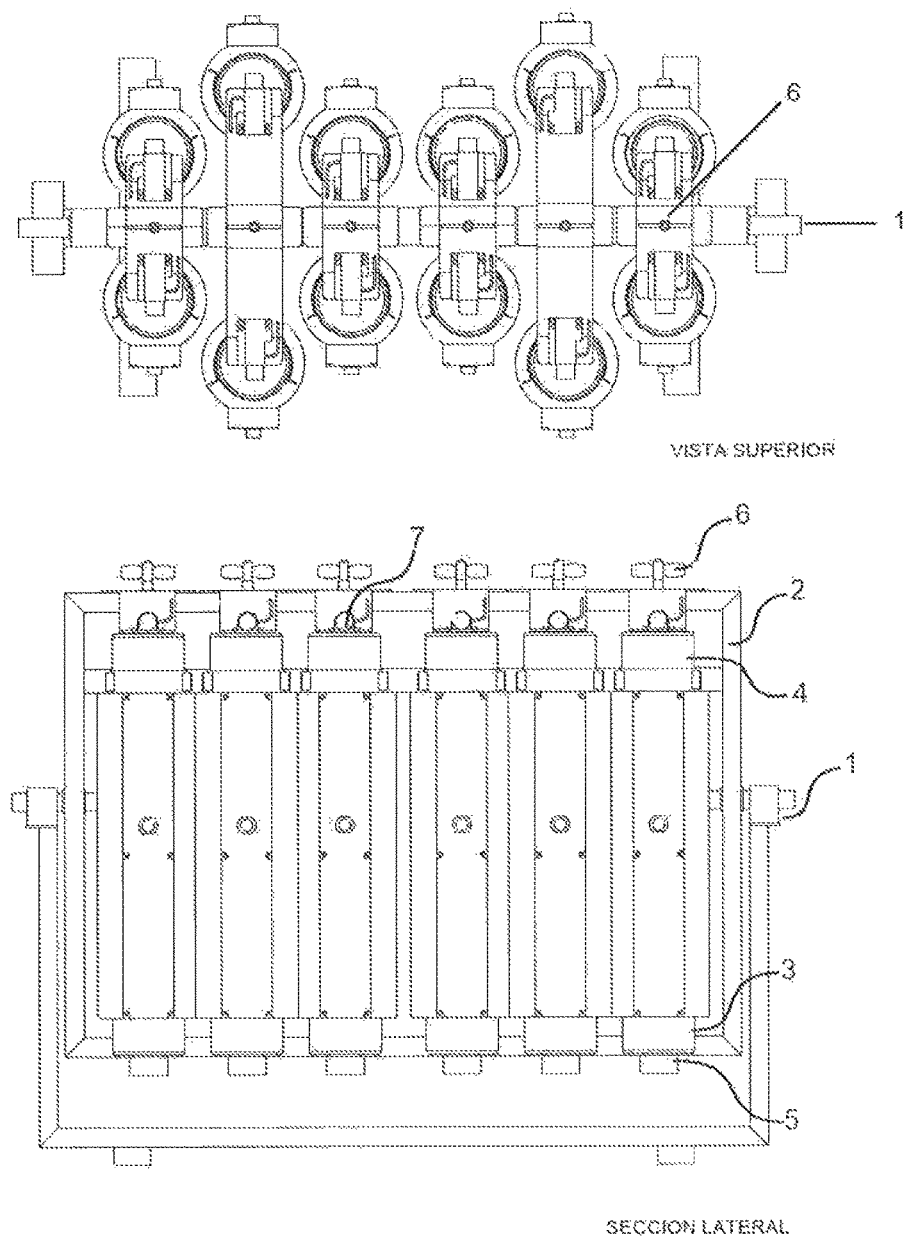
FIG. 1 presents the current prototype of 12 sedimentation cylinders designed for laboratory scale use, that was considered for the development of the control system and optimum sensor position. The rotational motor and rotational housing are not shown.
Figure 5:
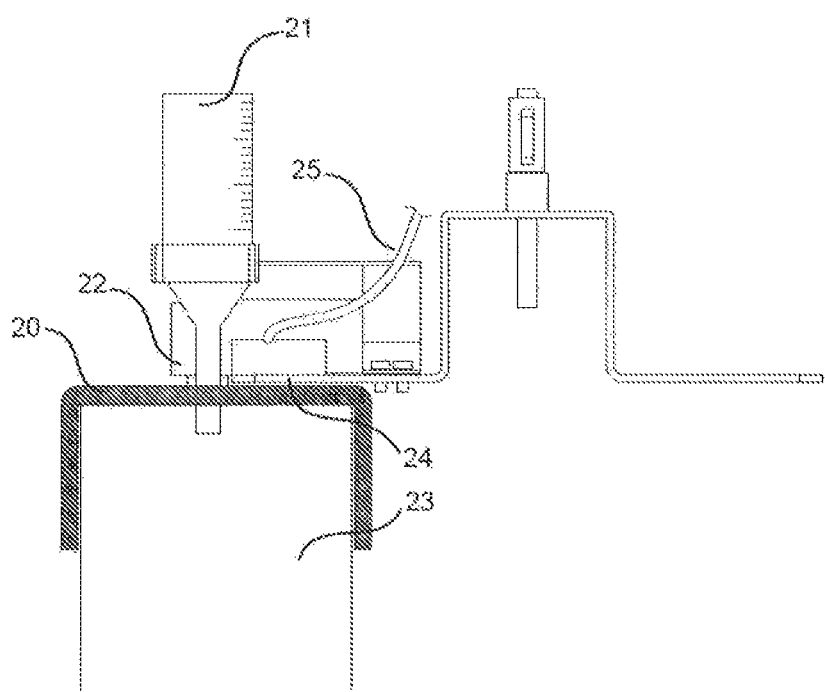
FIG. 5 presents the top sedimentation cylinder stopper layout for an electronic additive injection.

Referring to FIG. 1, a sedimentation apparatus housing 12 sedimentation cylinders is presented. The number of sedimentation cylinders, their dimensions and order of placement within the mixing apparatus can vary from the figure presented. The sedimentation cylinders presented in FIG. 1 do not show the sensors; those are presented in FIGS. 2 and 3 in more detail. The sedimentation cylinders and their sensor housing may be independently installed within the apparatus. Also not shown in FIG. 1 is the system to mix and rotate the apparatus. The rotation is made around an axis (1) whereby the support structure (2) can rotate 360 degrees if required, depending on the mixing operation required. Each sedimentation cylinder has a bottom stopper (3) and top stopper (4) where the bottom stopper (3) is mounted on a lateral bar by a fixing (5) to the supporting structure (2). The sedimentation cylinder is fixed in the supporting structure (2) by a clamping system (6) around the top stopper (4) whereby, but not limited to, two sedimentation cylinders can be mounted together. The top stopper (4) of each sedimentation cylinder has an additive injection system (7) that varies depending on the type and quantity of additive to be used, however, FIG. 5 presents a more generic electronic stopper system developed as part of the invention.

Using the control system, each sensor housing has an electronic identification tag so that the data can be logged from a specific sedimentation cylinder and be identified in the data. Prior to the start of the test, the control system requests that the user provide data relating to the properties of the material, origin and test parameters to be used for the test. The control system also checks that the sensors are operating correctly and the housings are correctly attached prior to the mixing stage.

The clamped structure is rotated around an axis controlled by the control system. The gyration sequence used can be modified as part of the control system. The mixing sequence is performed in a two stage process, firstly to ensure the pulp in the sedimentation cylinders is thoroughly mixed. The apparatus then stops at its vertical position and the chemical additives are added into the sedimentation cylinders. The user triggers the start of the second stage of mixing whereby the apparatus rotates and mixes the pulp and additives. The apparatus then stops at its vertical position and the settling test formally commences.

The displacement of the settling material is generally at its highest at the beginning of a test; hence the control system allows for the data collection frequency to be variable and therefore to allow for a higher frequency data sampling rate as required. The data collection frequency can be modified by the control system both locally or remotely as required.

Figure 2:
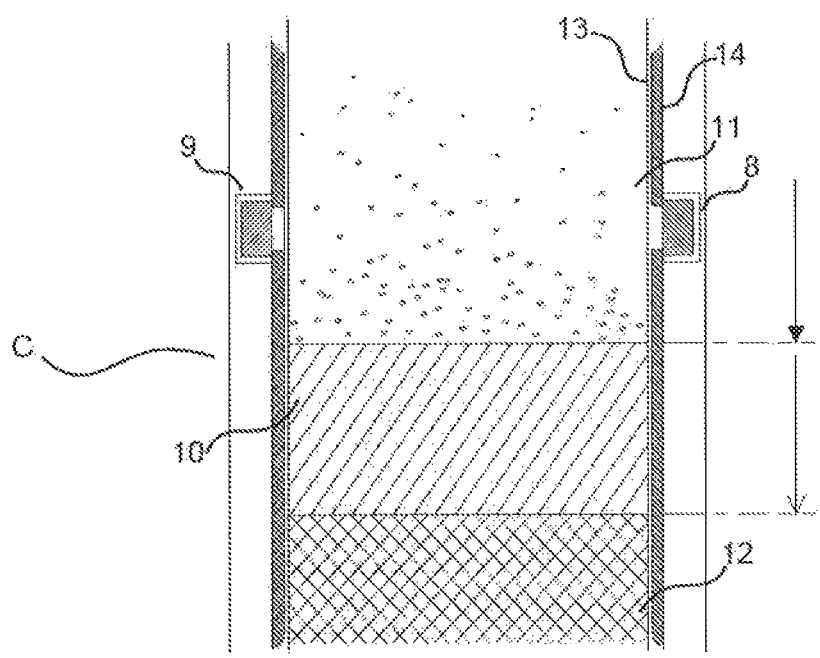
FIG. 2 presents the concept of the functionality of a single non-intrusive emitter and receiving sensor array mounted in a single sedimentation cylinder.

FIG. 2 presents the concept of the functionality of a single non-intrusive emitter (8) and receiving sensor array (9) mounted on the housing (C) of a single sedimentation cylinder for a solid-liquid settling scenario. The emitter sensor (8) transmits a fixed wavelength or variable wavelength that is received and processed by the receiving sensor (9). If the mud bed (10) is above the sensor position a calibrated reading is generated, and as the bed passes the receiving sensor the time is recorded and the wavelength intensity continuously monitored to establish the clarity of the liquor above the moving bed with time. Each sensor along the housing records the same information in a simultaneous form controlled by the control device to determine the settling bed position with time, the clarity of the liquor (11) at various depths above the moving bed, and the final settled mud bed height (12). The test normally runs for a period of 24 hours but can be modified by the control system both locally or remotely when required to run for different periods of time. The sedimentation cylinder wall (13) and internal wall (14) of the housing (C) are shown and preferable in contact. For liquid-liquid settling tests, the most dense liquid, or intermediate boundaries can be determined as they pass each sensor location.

Figure 3:
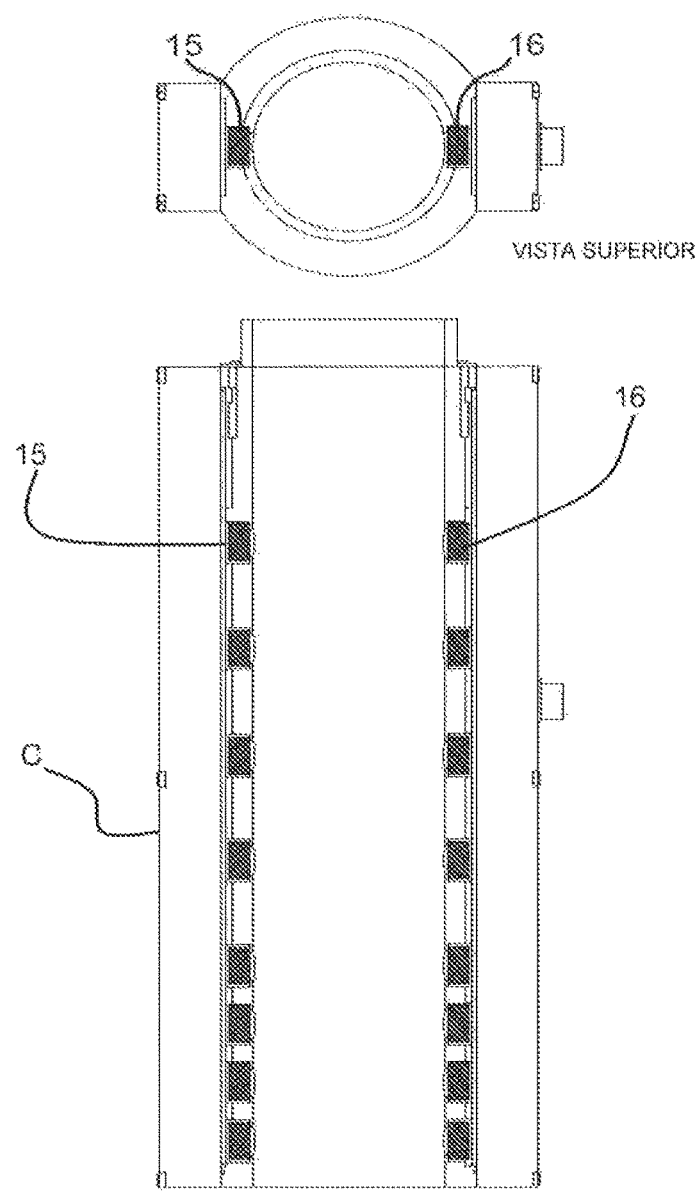
FIG. 3 presents a complete housing of the sedimentation cylinder used with 8 emitter and 8 receiving sensors.
Figure 4:
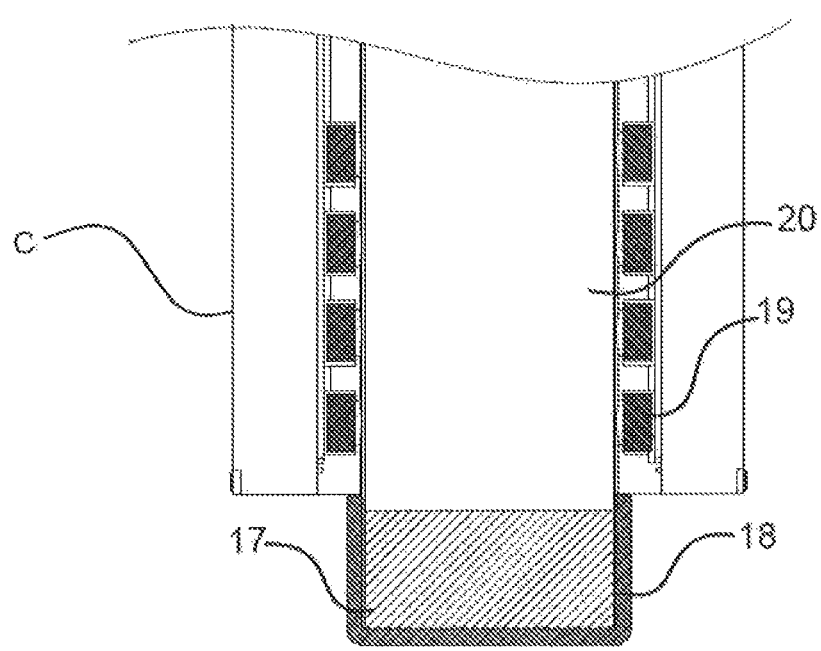
FIG. 4 presents the bottom sedimentation cylinder stopper layout to contain the settled slurry to facilitate removal of the solids portion following completion of the solid-liquid settling test.

FIG. 3 presents a housing (C) of a complete sedimentation cylinder, used with 8 emitter (15) and 8 receiving sensors (16) installed. The number and position varies depending on the sedimentation cylinder to be used and the type of material requiring testing. The housing (C) fits over the sedimentation cylinder containing the pulp and rests on the bottom stopper as shown in FIG. 4. Each housing (C) contains the sensors, electronic circuit boards, associated wiring, and the data connection to the main control system. Once positioned in the sedimentation apparatus, the housing and sedimentation cylinder with top and bottom stoppers is clamped into the apparatus. The top stopper, as shown in FIG. 5 with an electronic additive injection system, is used to contain the chemical additive, if required as part of the test. The additive is prepared and measured accordingly to be pre-installed in the injection system which is either activated by the user manually or automatically by the control system prior to the second stage of mixing. This top stopper and injection system is designed to allow the pulp and liquor contained in the sedimentation cylinder to wash all remnants of the additive from the container during the second stage of mixing, so as to ensure the entire additive has entered the pulp.

FIG. 4 shows the position of a final mud bed or dense liquid interface (17), the position of which varies depending on the characteristics of the solid-liquid or liquid-liquid mixture. The bottom stopper (18) is preferably made of natural rubber that can be removed from the sedimentation cylinder by the user. The height and width of the stopper vary depending on the sedimentation cylinder to be used and the type of material required for testing. The final sensor position (19) on the housing (C) varies depending on the type of solid-liquid or liquid-liquid mixture to be used. The liquor or liquid of lesser density (20) is contained in the sedimentation cylinder above the mud bed or liquid of higher density (17).

FIG. 5 shows the top stopper (20) with a generic additive injection system (21), which can be an electronic injection system comprising an electronic valve (22) permitting the additive to feed the sedimentation cylinder either by gravity or pressure. The height and width of the stopper vary, so as the injection system, depending on the sedimentation cylinder to be used, the type of material that requires testing, and chemical additive dosage required. The valve has to be 2 way to allow the backward flow of slurry or liquid to wash back into the additive container to ensure that all additive injection has entered the sedimentation cylinder (23). A support system (24) for the valve and additive container ensures that both said items can be removed with the rubber stopper (20).

The wires (25) can be disconnected from the control system, which controls the additive injection system. The electronic valve can correspond to a solenoid valve preferably a pressure valve which is controlled by the control system.

An alternative to the electronic injection system as shown in FIG. 5 is a manual injection system of quick release by button release or syringe style applications. This is operated by the user prior to the second mixing stage and start of the settling test. The electronic system is preferred to improve the accuracy of the additive injection by allowing for the simultaneous operation of each sedimentation cylinder.

The emitter sensors are all powered by a common rail that is fed from the same power source as the control system.

The control system, as per present day technology but not limited to, is currently based on a Linux operating system and is a self-contained equipment that accompanies the apparatus and is operated by the HMI, and input devices as preferred by the user (optical device and keyboard). The computer, when connected to the internet by cable or wireless, can be remotely accessed to perform a variety of tasks including, but not limited to, diagnosing in real time the sedimentation test through sensors, accessing and manipulating stored test data results, modifying sedimentation cylinder identification data and changing remote communication and data upload parameters. The system is designed to process and upload or distribute the data electronically to a third party user or server for further analysis and processing. The user or client then receives the presentation of the interpreted data via electronic means or remote server access.

The control system may incorporate connections to log data from additional intrusive sensors installed in each sedimentation cylinder. These sensors may measure, in parallel with the housing sensors, other slurry properties including but not limited to, pH, temperature, oxidation reduction potential, and conductivity. These sensors each have an electronic identification to allow the computer to record the sedimentation cylinder location and group its data with the corresponding receiving sensors.

At the end of the test, the sensor housing and contained sedimentation cylinders are unclamped and carefully removed from the apparatus. The housing is removed and the liquor from each sedimentation cylinder can be extracted to leave the solids at the base of the sedimentation cylinder. The bottom stopper is carefully removed to access the solids for further testing such as, rheology, particle size distribution, specific gravity, plasticity limits, and any other mineral or liquid characterization techniques.

Due to modern advances in technology, it is envisaged that the same sensor control, data collection and processing methods can be integrated on more compact, reliable technology platforms so as to improve the operation of the apparatus in the future.

The invention claimed is:

1. Apparatus for static sedimentation tests comprising a plurality of sedimentation cylinders, which are subject to the same mixing conditions, said apparatus comprises:
   a. A plurality of transparent sedimentation cylinders;
   b. Each sedimentation cylinder is located inside a non-intrusive emitter and receiving sensor housing where each housing has an electronic ID card, electronic circuit boards and connection to a control system;
   c. A support structure containing the sedimentation cylinders and sensor housings which rotates around an axis of rotation;
   d. Each sedimentation cylinder has a bottom stopper and top stopper;
   e. Where each bottom stopper of each sedimentation cylinder is mounted on a lateral bar parallel to the rotation axis, by a fixing to the supporting structure;
   f. Also the sedimentation cylinders are fixed in the supporting structure by a clamping system around the top stopper of each sedimentation cylinder;
   g. The top stopper of each sedimentation cylinder has an additive injection system.

2. Apparatus according to claim 1, wherein the additive injection system is a quick release injection system that can be activated manually or by the control system.

3. Apparatus according to claim 2, wherein said sensors are sensors to sense mud bed position, final mud bed height, solids density, liquid density and clarity of the liquor.

4. Apparatus according to claim 3, wherein said non-intrusive receiving sensors are selected from the group comprising photosensors, IR, UV, optical or wavelength based sensitivity sensors and said non-intrusive emitting sensors are selected from the group comprising, Light Emitting Diode (LED), IR, UV, laser or fixed/variable wavelength emitter.

5. Apparatus according to claim 4, wherein each housing is equipped with at least 4 emission wavelength sensors and with at least 4 reception wavelength sensors, facing each other and spaced at varying distances (depending on the type of the material under test) along the housing body.

6. Apparatus according to claim 5, wherein the sensors of each housing are connected to a control system, which records information of each sensor relative to the mud bed position and/or consolidation over time or the interfaces between two liquids with different densities.

7. Apparatus according to claim 6, wherein in addition, each sedimentation cylinder has at least a sensor installed within the slurry (intrusive sensors) to measure at least one of the group consisting of pH, temperature, oxidation reduction potential, conductivity of the suspension that is subjected to the sedimentation tests, and combinations thereof, whose data is recorded in parallel to data of the non-intrusive sensors by the control system.

8. Apparatus according to claim 7, wherein the housings with their sedimentation cylinders are located outwardly of the support structure and the sedimentation cylinder wall and internal wall of the housing are in contact.

9. Apparatus according to claim 8, wherein the clamping system around the top stopper, mount together two sedimentation cylinders to the rotational axis.

10. Apparatus according to claim 9, wherein the housing of each sedimentation cylinder rests on the bottom stopper of the sedimentation cylinder, stopper which is made of natural rubber and can be easily removed from the sedimentation cylinder, after the sedimentation test, to easily access the settled solids.

11. Apparatus according to claim 10, wherein the control system is connected to intrusive and non-intrusive sensors and collects and interprets data delivered by sensors; further provides the status of the sensors, the control system also communicates, processes, records and stores data from sensors in real time.

12. Apparatus according to claim 11, wherein the control system also provides real-time diagnostics through sensors of the sedimentation tests, and upload or distributes the data to a storage media, a computer or a server, wherein the diagnosis of the control system consists in inform whether the connection of the sensors is correct, if the operation of the sedimentation cylinders is correct or the status of each sedimentation cylinder during the sedimentation test.

13. Apparatus according to claim 12, wherein the control system is also connected to a remote server or data storage system via the internet by cable or wireless communication whereby the data collected by the sensors is evaluated and processed remotely on a third party server and then results are sent via electronic form or by remote server access by the user.

14. Apparatus according to claim 12, wherein the control system is also connected and controlled by a Human Machine Interface (HMI) to allow initial data regarding the physicochemical properties of the slurry from the sedimentation test and chemical additive contained in each sedimentation cylinder are registered, where the HMI also controls the operation of the sedimentation test.

15. Apparatus according to claim 1, wherein the plurality of transparent sedimentation cylinders is 12.

16. Method for static sedimentation tests carried out simultaneously and under the same mixing conditions in a plurality of sedimentation cylinders, said method comprises:
   (i) Add a solution which sedimentation tests are required to be performed to a plurality of transparent sedimentation cylinders, where each sedimentation cylinder is located inside a non-intrusive emitter and receiving sensor housing, where the sensor housings are supported in a support structure which rotates around an axis of rotation and each sedimentation cylinder has a bottom stopper and top stopper, where the top stopper has an additive injection system;
   (i) Rotate the sedimentation cylinders around an axis of rotation to homogenise the solutions in each sedimentation cylinder;
   (ii) Stop upright the sedimentation cylinders and add chemical additives to each sedimentation cylinder,
   (iii) Rotate again the sedimentation cylinders around the axis of rotation, for mixing the solutions and additives;
   (iv) Stop upright the sedimentation cylinders;
   (v) Start the sedimentation test;
   where all data from sedimentation tests and data delivered by each non-intrusive sensors with respect to mud bed position and/or consolidation time, final mud bed height, solids density, liquid density or clarity of the liquor are recorded by a control system.

17. Method according to claim 16, wherein the plurality of sedimentation cylinders is 12 and also have intrusive sensors and the method also includes measurement of pH, temperature, oxidation reduction potential, and conductivity of the suspension of those sensors whose data is recorded in parallel to data of the non-intrusive sensors by the control system.

18. Method according to claim 17, wherein at the end of the sedimentation tests, the sensor housing and contained sedimentation cylinders are unclamped and removed from the support structure, the top stopper is removed to access the liquor from each sedimentation cylinder leaving the solids at the base of each sedimentation cylinder, the bottom stopper is removed so the solids can be extracted for further tests.

19. Method according to claim 18, wherein the further tests are selected from at least one of rheology, particle size distribution, specific gravity, plasticity limits, or liquid or characterization techniques of mineral or liquid.

20. Method according to claim 19, wherein the control system can communicate, process, interpret, diagnose, record and store data from intrusive and non-intrusive sensors, in real time, distributing the data electronically to a computer or server, that may be a remote server.

21. Method according to claim 20, wherein the control system diagnoses whether the connection of the sensors is correct, if the operation of the sedimentation cylinders is correct or the status of each sedimentation cylinder during the sedimentation test.

22. Method according to claim 21, wherein the data collected by the sensors is evaluated and processed remotely on a third party server by sending via electronic form or by remote server access by the user wherein the remote server is connected to the control system via the internet by cable or wireless communication.

23. Method according to claim 22, wherein said control system is connected and controlled by a Human Machine Interface (HMI) to allow initial data being registered regarding the physicochemical properties of the slurry from the sedimentation test and the chemical additive to be used.

* * * * *